United States Patent
Persyn et al.

(10) Patent No.: US 8,361,012 B2
(45) Date of Patent: Jan. 29, 2013

(54) DRY TO WET INJECTOR

(75) Inventors: Joseph T. Persyn, Lakehills, TX (US); Joseph A McDonough, Helotes, TX (US); James D Oxley, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 843 days.

(21) Appl. No.: 12/502,713

(22) Filed: Jul. 14, 2009

(65) Prior Publication Data

US 2011/0015568 A1 Jan. 20, 2011

(51) Int. Cl.
*A61M 37/00* (2006.01)

(52) U.S. Cl. .................................................. 604/92

(58) Field of Classification Search ............... 604/82, 604/92
See application file for complete search history.

(56) References Cited

U.S. PATENT DOCUMENTS

| | | | |
|---|---|---|---|
| 4,002,474 A * | 1/1977 | Blachford | 419/36 |
| 4,106,932 A * | 8/1978 | Blachford | 75/252 |
| 4,329,988 A | 5/1982 | Sarnoff et al. | |
| 4,401,432 A | 8/1983 | Schwartz | |
| 4,404,828 A * | 9/1983 | Blachford | 72/42 |
| 4,515,586 A | 5/1985 | Mendenhall et al. | |
| 4,548,598 A * | 10/1985 | Theeuwes | 604/85 |
| 4,985,017 A * | 1/1991 | Theeuwes | 604/92 |
| 5,069,671 A * | 12/1991 | Theeuwes | 604/251 |
| 5,092,843 A | 3/1992 | Monroe et al. | |
| 5,681,291 A | 10/1997 | Galli | |
| 5,755,688 A * | 5/1998 | Piontek et al. | 604/83 |
| 6,149,626 A | 11/2000 | Bachynsky et al. | |
| 6,221,893 B1 | 4/2001 | Hellstrand et al. | |
| 6,451,335 B1 * | 9/2002 | Goldenheim et al. | 424/426 |
| 6,641,561 B1 | 11/2003 | Hill et al. | |
| 6,656,150 B2 | 12/2003 | Hill et al. | |
| 6,702,778 B2 | 3/2004 | Hill et al. | |
| 6,770,052 B2 | 8/2004 | Hill et al. | |
| 6,953,445 B2 | 10/2005 | Wilmot et al. | |
| 7,011,649 B2 | 3/2006 | De La Serna et al. | |
| 7,329,235 B2 | 2/2008 | Bertron et al. | |
| 7,351,220 B2 | 4/2008 | Chiwanga et al. | |
| 7,390,319 B2 | 6/2008 | Friedman | |
| 7,416,540 B2 | 8/2008 | Edwards et al. | |
| 7,416,570 B2 | 8/2008 | Suzuki et al. | |
| 7,927,618 B2 * | 4/2011 | Bodmeier | 424/423 |
| 2008/0277596 A1 * | 11/2008 | Oxley | 250/462.1 |
| 2011/0015568 A1 * | 1/2011 | Persyn et al. | 604/92 |

* cited by examiner

*Primary Examiner* — Nicholas Lucchesi
*Assistant Examiner* — Diva K Chander
(74) *Attorney, Agent, or Firm* — Grossman, Tucker et al

(57) ABSTRACT

The present disclosure relates to an apparatus and method for combining a solid particulate with a solvent prior to an injection protocol within an injector device. The solid particulate may be a pharmaceutical compound and the microcapsules contain a solvent for such particulate. Upon application of pressure, the microcapsules may be configured to burst and release the solvent, thereby dispersing and/or partially dissolving the particulate. The injector therefore allows for the use of relatively unstable pharmaceutically active compounds in a device that requires relatively long storage times and the use of pharmaceutical compounds that are relatively stable in the dry state.

25 Claims, 6 Drawing Sheets

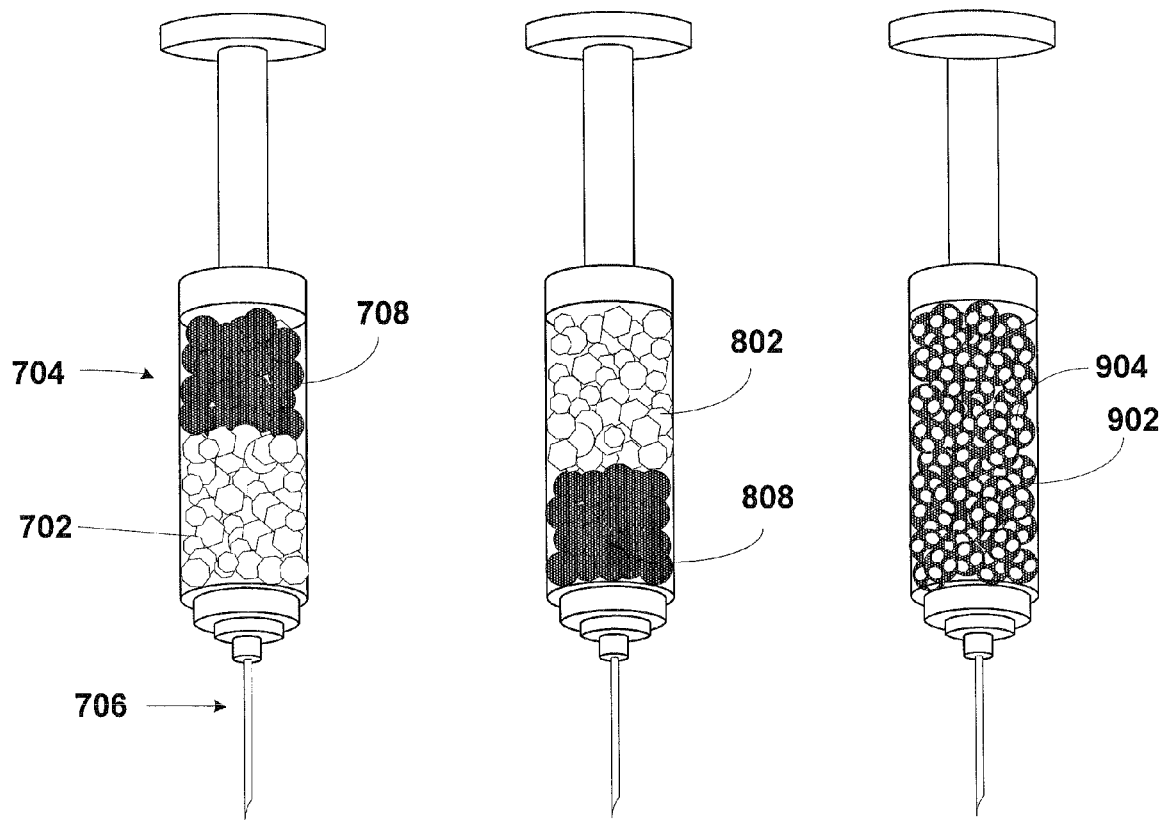
*FIG. 7*  *FIG. 8*  *FIG. 9*

DRY TO WET INJECTOR

FIELD OF THE INVENTION

The present disclosure relates to a dry to wet injector for injection of solid solute material through an injection device. In particular, the injector may include microcapsules containing solvent or heterogeneous phase material such as a hydrogel containing selected levels of solvent. Upon application of injection pressure, the capsules may be ruptured allowing solvent and solid to mix prior to exiting the syringe. The present invention may therefore provide a microcapsule/solute apparatus for point of use solubilization.

BACKGROUND

Pre-loaded syringes have been utilized to deliver pharmaceuticals in a variety of applications. Common off the shelf (COTS) auto injectors may be used in household, hospital and military environments. For example, in emergency situations, pre-loaded auto injectors have been used for self-administration of epinephrine or atropine. In addition, the pre-loaded syringes may be stored for various amounts of time, such as days, weeks, months and sometimes even years. However, some pharmaceuticals, including, for example, various vaccines, antigens, genes and butyrylcholinesterase (BChE), may be insoluble in aqueous solutions or may degrade upon exposure to aqueous solutions over a period of time. Harsh solvents, such as dimethyl sulfoxide (DMSO) or aqueous solutions exhibiting a relatively acid or basic pH may be needed to facilitate injection of these pharmaceuticals. However, such solvents and/or solutions may cause undesirable or painful side effects.

SUMMARY OF THE INVENTION

An aspect of the present disclosure relates to an injector allowing for the combination of a solvent and a solid comprising a housing containing a solid particulate, wherein the solid particulate has a diameter of 0.1 microns to 5.0 mm. The housing also includes microcapsules containing a solvent for the particulate and/or a heterogeneous phase material including such solvent. The microcapsules may have an average mean particle size of 100 nm to 10,000 microns and are configured to open upon application of pressure.

Another aspect of the present disclosure relates to injector allowing for the combination of a solvent and a solid comprising a housing containing a solid particulate of a pharmaceutical substance, wherein the pharmaceutical substance has a diameter of 0.1 microns to 5.0 mm. The housing also contains microcapsules containing a solvent for the particulate or a heterogeneous phase material including such solvent. The microcapsules have an average mean particle size of 100 nm to 10,000 microns and are configured to open upon application of pressure and the solid particulate is capable of dissolving in the solvent within the time period of less than or equal to 10 seconds and the microcapsules are also configured to open upon application of a pressure of 10 psi to 5000 psi.

A still further related aspect of the present disclosure includes a method for injection of a pharmaceutical comprising supplying an injector including a housing for solid particulate, wherein the solid particulate has a diameter of 0.1 microns to 5.0 mm. The housing also includes microcapsules containing a solvent for the particulate and/or a heterogeneous phase material including such solvent. The microcapsules have an average mean particle size of 100 nm to 10,000 microns and are configured to open upon application of pressure. This may be followed by applying pressure to the microcapsules thereby causing the microcapsules to open and release the solvent wherein the pharmaceutical particulate is dispersed and/or partially dissolves in the solvent.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIG. 7 is another partial cut-away view of a syringe in accordance with the present disclosure, illustrating the possible placement of a pharmaceutical particulate with the indicated microcapsules.

FIG. 8 is another partial cut-away view of a syringe in accordance with the present disclosure illustrating another possible placement of a pharmaceutical particulate with the indicated microcapsules.

FIG. 9 is another partial cut-away view of a syringe in accordance with the present disclosure illustrating another possible placement of a pharmaceutical particulate with the indicated microcapsules, and in particular, the coating of the pharmaceutical on the microcapsules.

DETAILED DESCRIPTION

Figure 1:
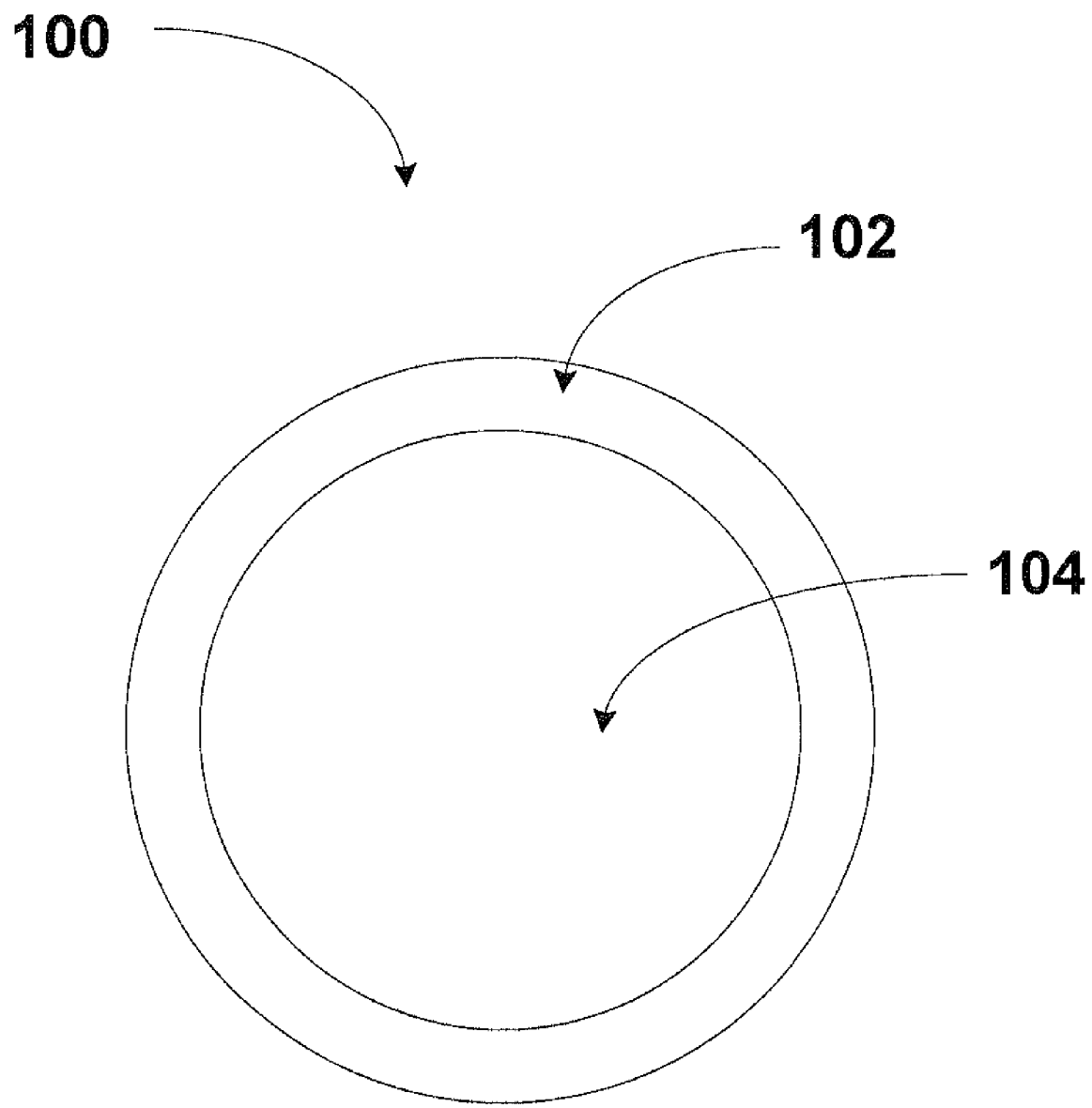
FIG. 1 is a perspective view of the microcapsules disclosed herein.

It is to be understood that this disclosure is not limited in its application to the details of construction and the arrangement of components set forth in the following description or illustrated in the drawings. The embodiments herein are capable of other embodiments and of being practiced or of being carried out in various ways. Also, it is to be understood that the phraseology and terminology used herein is for the purpose of description and should not be regarded as limiting.

Commonly, pharmaceutical substances or compounds are administered parenternally, i.e., by injection or infusion, may be liquid or provided in an aqueous solution allowing for injections or infusions to be delivered into the bloodstream, muscles, skin, under the skin, the heart, spinal canal, etc. Furthermore, these substances may be stored as a liquid or in aqueous solution in syringes or IV bags. However, when pharmaceutical substances are liquid insoluble, e.g., water insoluble or degrade upon exposure to water, it may be appreciated that it may be difficult to store or administer these pharmaceutical substances in a parenteral manner. Solvents such as dimethyl sulfoxide or aqueous solutions exhibiting extreme pH numbers (i.e., 5 or less or 9 or greater) may be necessary to store and/or deliver these pharmaceutical substances, which may cause relatively undesirable or harmful side effects including pain.

The present disclosure relates to an apparatus and method for dispensing a solvent/solute composition. The solvent composition may be formed by first providing microcapsules containing a solvent or a heterogeneous phase material such as a hydrogel containing a selected level of solvent. The microcapsules may then be combined with a solid solute particulate, such as a selected pharmaceutical compound, or mixtures of pharmaceuticals, and the microcapsules, upon release of the solvent and/or the heterogeneous phase material, within a suitable injector, provides a solvent composition that may be acceptable for a given injection protocol.

Preferably, the solvent may be water, but other solvents are contemplated herein, and in particular, those solvents that are suitable to serve as a pharmaceutically acceptable carrier. The solvent may therefore be one that fully or partially dissolves the solute particulate (e.g. the pharmaceutical substance) and one which is acceptable for use in a parenternal injection protocol. For example, the pharmaceutical may have a solubility in the solvent at a level of 0.1% (wt.) to 99.9% (wt.), including all values therein, in 0.1% increments. The solvent may also be preferably selected such that it may dissolve the solid particulate within the time period of less than or equal to 10.0 seconds. More preferably, solubilization may occur within the time period of 0.1 seconds to 10.0 seconds at 0.1 second increments. Even more preferably, the time period is such that the solid particulate may be solubilized within the time period of less than or equal to 2.0 seconds. Furthermore, the dosage level that may be achieved within any of the aforementioned time periods is configured such that it is less than or equal to 600 mg/ml, more preferably between 1 microgram (μg) to 600 mg/ml at 1.0 mg/ml intervals, and even more preferably, between 200 mg/ml to 400 mg/ml.

As noted, the pharmaceutical may be in the solid state, and in particulate form. Such particulate form may have a diameter (maximum linear dimension through the particle) of 0.10 microns (μm) to 5.0 mm. The particulate may therefore assume a variety of geometrical configurations, such as round, spherical, trapezoidal, rectangular, square, triangular, hexagonal, elongated etc. With respect to an elongated form, the particulate may have a length (L) that exceeds its diameter (D). In addition, the particulate may include a mixture of any of the above.

A pharmaceutical substance herein may be understood as herbs, vitamins, or other natural or synthetic chemical substances utilized in the treatment, prevention, cure or diagnosis of infections or disease or to enhance physical or mental well being. Pharmaceuticals may therefore include antibiotics, vaccines, antigens and genes, such as butylcholinesterase (BChE), and mixtures thereof. In some examples, the pharmaceutical may include substances that may be water insoluble or may not dissolve to an acceptable level to provide an aqueous carrier solution. In such a situation, as alluded to above, the solvent may be selected such that it is not water based, but still otherwise acceptable to provide the indicated dissolution and dosage within the indicated time periods.

More specifically, the pharmaceutical that may be utilized herein includes, but is not limited to oximes, which may be understood as compounds including

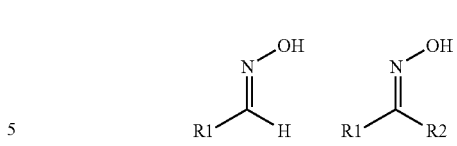

where R1 is an organic side chain (i.e. a side chain containing one or more carbon atoms) and R2 is either hydrogen forming an aldoxime or another organic group forming a ketoxime. In particular, the pharmaceutical herein may include a 1,1'-methylenebis[4-(hydroxyimino)methyl]-pyridinium salt, which may be represented by the following general formula:

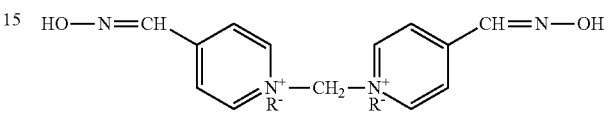

where R may be a halide counter-anion such as a halogen (e.g. Cl⁻ or Br⁻ or I⁻) in which case the compound may be referred to as "MMB4 Dihalide.". More generally, R may be derived from a salt of an inorganic or organic acid. For example, the anion may be derived from hydrogen sulfate ($H_2SO_4$), nitrate, fumarate, lactate, tartate, citrate, and/or acetate. In addition, R may be a counteranion such as an alkyl sulfonate group. In such a case, the 1,1'-methylenebis[4-(hydroxyimino)methyl]-pyridinium salt would assume the following general formula:

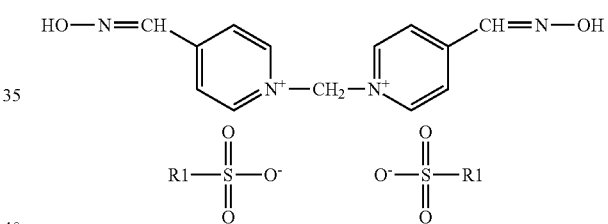

wherein R1 may be selected such that it does not interfere (e.g. steric interference) with the formation of the particular polymorphic pyridinium salts noted below. Accordingly, R1 may be a methyl (—$CH_3$) group, and it is contemplated herein that it may also include ethyl type group functionality (—$CH_2CH_3$).

The oximes herein may therefore include (HI6, 2PAM, HLo7, MMB4) and atropine, or oximes and antimuscarnics (such as atropine) or BChE with one or more oximes and atropine. An antimuscarnic may be understood as a muscarinic receptor antagonist that reduces the activity of the muscarinic acetycholine receptor. The pharmaceuticals may therefore include HI6 in combination with atropine; 2-HI6, atropine and avisofone; MMB4 and atropine as well as any of the noted oximes in combination with Huperzine.

The pharmaceutical may also specifically include substances that may ultimately degrade upon exposure to a given solvent, such as water, wherein chemical or physical changes may occur to the substances causing a reduction in its effectiveness or activity.

Accordingly, one advantage herein is that the mixing of such substances with a given solvent occurs almost immediately prior to injection, thereby minimizing the time for degradation that may otherwise occur should one attempt to store such pharmaceutical in the solvent for any extended period of time (e.g., equal to or greater than 60 minutes). Accordingly, the disclosure herein may be particular applicable for a pharmaceutical whose pharmacological effectiveness once combined with a given solvent may be otherwise compromised and reduced.

As noted above, the pharmaceutical may be present in solid form. In addition, the pharmaceutical may be coated or otherwise treated with a functionalizing agent that may increase the solubility of the pharmaceutical within a given solvent after the solvent has been released from the microcapsules. The functionalizing agent may be a surface active agent or a dispersant. A surface active agent may be understood as an organic amphiphilic compound, containing hydrophobic groups and hydrophilic groups, and which lower the surface tension of the solvent that may be within the microcapsules. Furthermore, other methods contemplated to increase the solubility of the pharmaceutical within a given solvent may include providing the pharmaceutical in relatively smaller particulate form, mixing the pharmaceutical with a more rapidly dissolving excipient, such as a sugar (sucrose, lactose and/or fructose), salt (sodium chloride) or hydrocolloid.

It is also useful to note that the pharmaceutical may be combined with other excipients to enhance the stabilization of the pharmaceutical while in solid form and in storage. This may be particularly applicable in the case of biologically-based pharmaceutical active agents such as proteins or enzymes.

As now illustrated in FIG. 1, the microcapsules 100 may include a shell 102 and a core 104. The core may contain a liquid or solvent, including water or other appropriate solvent carrier. The solvent may be selected such that it provides a relatively low viscosity, such as in the range of 0.01 centipoise to 200 centipoise, including all values and increments therein. For example, the solvent may have a viscosity in the range of 0.1 centipoise to 4 centipoise, 50 centipoise to 100 centipoise, etc. As alluded to above, the solvent may include water, or water in combination with a water soluble solvent. The solvent may also include those solvents that are pharmacological acceptable carriers, and acceptable for injection purposes.

Furthermore, the core may contain a heterogeneous phase material (solid-liquid) such as a heterogeneous network of polymer chains that are water insoluble, wherein water is dispersed therein at a level of 50% by weight or higher, such as in the range of 50% by weight to 99% by weight, including all values therein, in 1.0% by weight increments. Accordingly, a heterogeneous phase material herein may be understood as network of solid and insoluble material that may contain dispersed solvent, which the solvent is again selected as a carrier for the solid particulate that is present for delivery or injection. In particular, one may employ a hydrogel which may be understood as a network of polymer chains that are solvent insoluble (e.g. water insoluble) which may be due to the presence of crosslinking. Representative polymers contemplated for use include poly(vinyl alcohol, sodium polyacrylates, acrylate polymers and copolymers containing hydrophilic functionality such as poly-2-hydroxylethylmethacrylate, poly(acrylamides), or mixtures thereof.

In addition, the solvent within the microcapsules may be configured to themselves provide pharmacological activity, as disclosed herein. Moreover, aside from including excipients with the pharmaceutical, one may include excipients to the core (solvent) material. Examples of excipients may again include sugar, salt, hydrocolloids, as well as dyes, dispersants, etc. Dyes may be radiopaque, luminescent, etc. It may therefore be appreciated that the release of a dye may then provide visual confirmation that the solvent has been released from the microcapsules, and that injection may then proceed.

The microcapsules may be formed by a number of physical and or chemical methods. Such methods may include coextrusion, rotating disk atomization, fluid bed coating, reverse phase interfacial polymerization, complex coacervation or ionic gelation. For example, in coextrusion, a concentric annular jet system may be used to extrude water through an inner nozzle and a coating material through an outer nozzle. As the liquid exits the nozzle, the coating material and liquid break up into core-shell droplets. The shell material may then harden, forming microcapsules.

The microcapsule shell composition may include, for example, thermoplastics, thermosets, waxes (polymeric material with Mn values of $\leq$2500) or fatty acids. In some examples the shell composition may include polyurethane, polyurea, polyesters, gum arabic, etc. It is also contemplated herein that the shell may itself be formed from those materials that avoid the need to be filtered prior to injection, in the sense that the materials are biodegradable and capable of being processed within the physiological environment. For example, the shell material may be one that is either digestible within a given subject (human) or be sourced from a material that may be passed without incident. Such material may therefore include poly(lactide), poly(glycolide), poly(lactide-glycolide) copolymers, polycaprolactones, polyanhydrides, glycerides, fatty acids, cellulose derivatives, as well as blends of any of the foregoing.

The microcapsules, including any coatings, and/or the excipients may have an average mean particle size (i.e., largest linear dimension) in the range of 100 nm to 10,000 μm, including all values and increments therein, such as in the range of 50 nm to 10 μm, 50 μm to 250 μm, etc. It may be appreciated that the microcapsules size may be adjusted depending upon a number of factors, such as the inner diameter of the delivery device, (i.e., a hypodermic needle, catheter, etc.).

Figure 2:
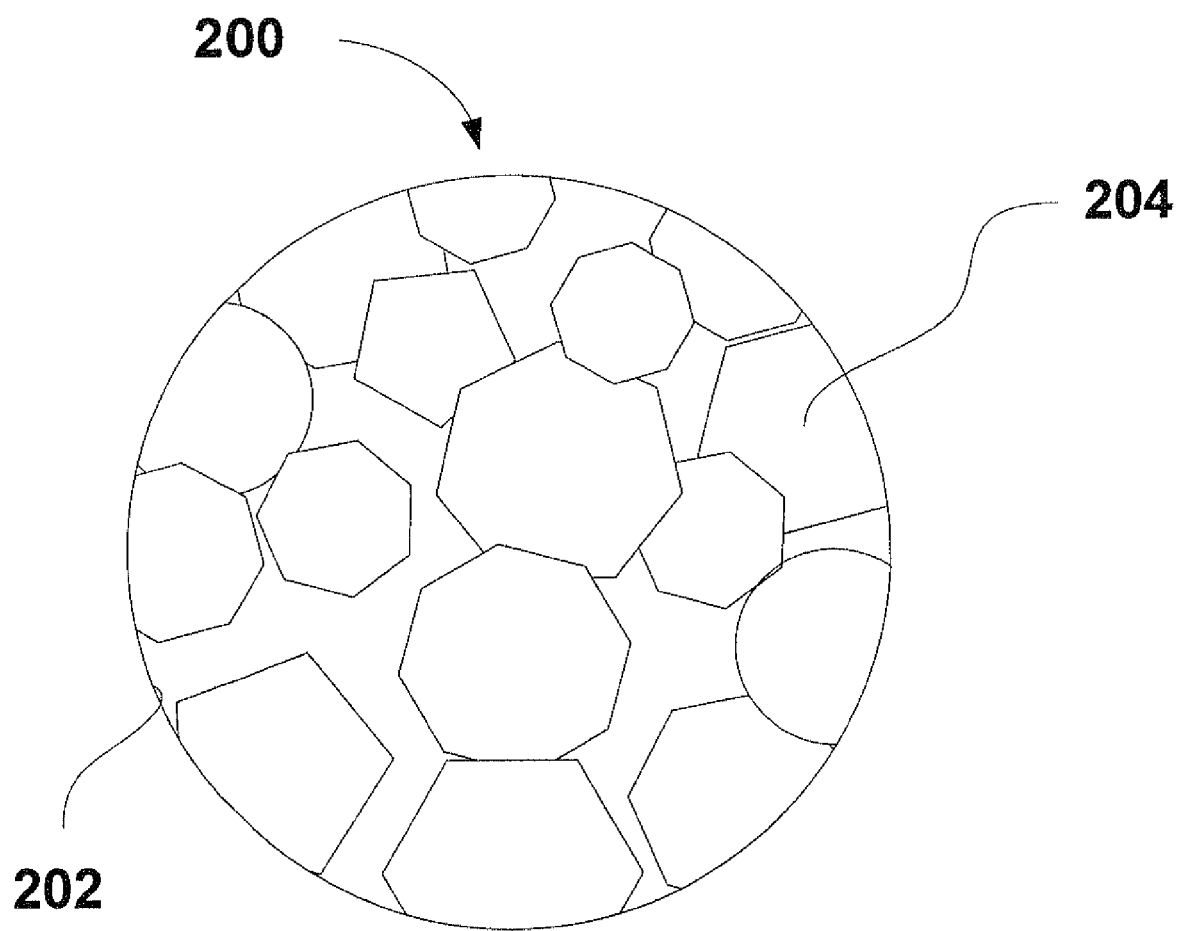
FIG. 2 is perspective view of the surface of a microcapsule, illustrating coating with a solid pharmaceutical.

The pharmaceutical may also be advantageously applied to the surface of the microcapsules or formulation into the microcapsule shell surfaces. For example, as illustrated in FIG. 2, the shells 202 of microcapsules 200 may be coated with the pharmaceutical 204. In another example, the pharmaceutical may be incorporated with and through the shell thickness. For example, the pharmaceutical may be dispersed in a gradient through the thickness of the shell or localized to specific surfaces of the shell, i.e., the interior or exterior surfaces. The gradient may be such that a relatively higher concentration of the pharmaceutical is on the surface of the microcapsule, so that on the interior shell surface of the microcapsule, which is then in contact with a given solvent, no pharmaceutical is present. In such manner, as noted above, the activity of the pharmaceutical is still preserved.

Figure 3:
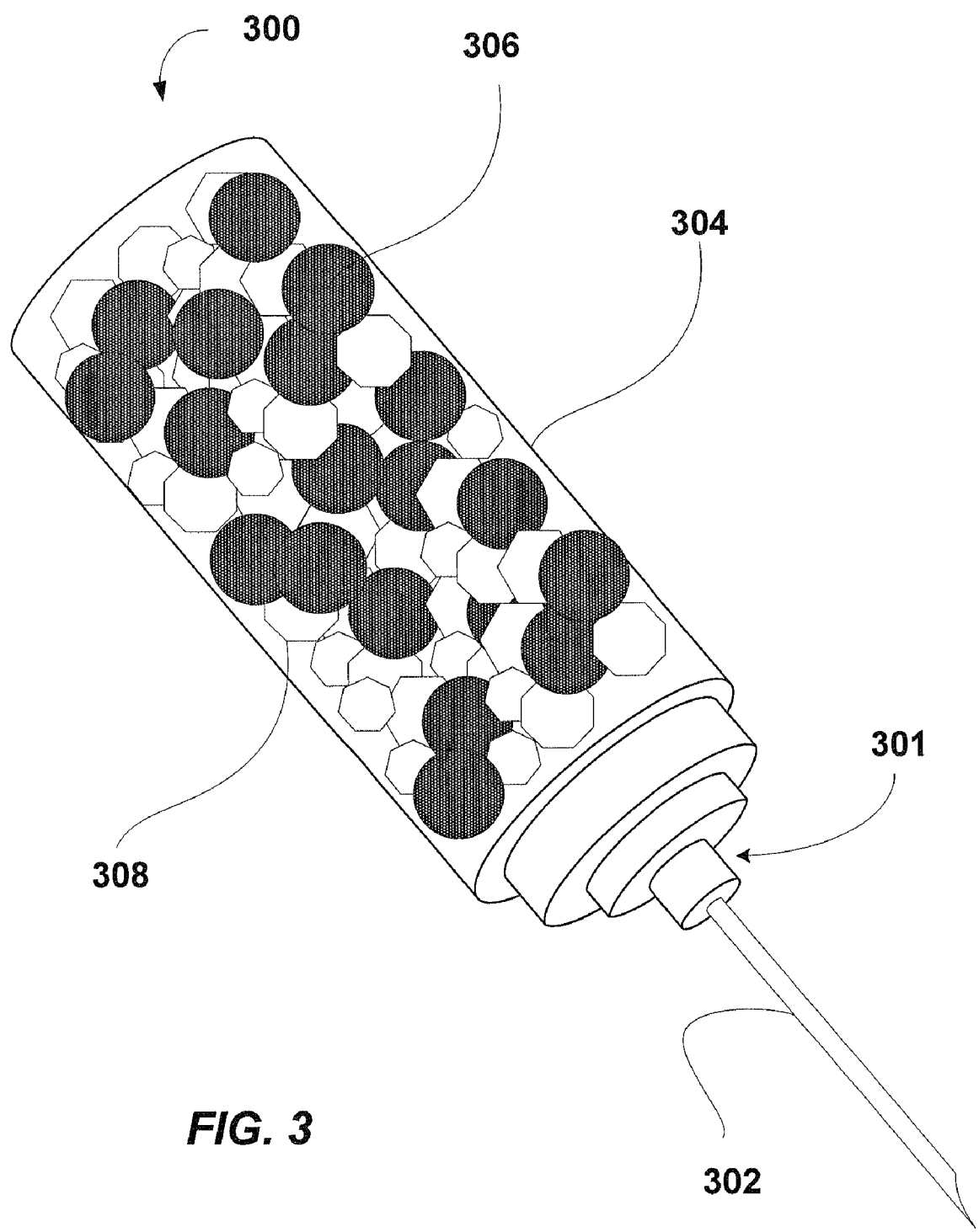
FIG. 3 is a partial cut-away view of a syringe in accordance with the present disclosure.

The composition, including the pharmaceutical and the microcapsules, may be loaded into a container, such as an IV bag or a syringe, including, for example, auto injector syringes. Examples of auto injector syringes may include, for example, those described in U.S. Patent Nos. 5,681,291, 6,221,893, 7,351,220, 7,390,319, or 7,416,540, the disclosures of which are incorporated herein by reference. However, as alluded to above, common off the shelf auto injectors have stability problems as the active pharmaceutical ingredient (API) will tend to degrade in water or other liquid carrier. As a result, effective potent medicines may not be used in auto injectors. Furthermore, relatively strong solvents such as DMSO or extreme pH solutions may otherwise be employed to facilitate injection which may trigger painful side effects. The present invention therefore provides, among other things, a more efficient injection of APIs with respect to water unstable or water insoluble agents.

FIG. 3 illustrates one example of a syringe 300 including an outlet portion 301 the may be attached to a hypodermic needle 302. The plunger portion is not shown in this particular illustration. It is therefore again worth noting that while the invention herein is illustrated with respect to such a syringe, the invention herein applies to any injector configuration capable of handling the microcapsule/solvent combination. With that qualification, it may be noted that the housing of the syringe 304 may be filled with a composition of microcapsules 306 and pharmaceutical 308. Although the pharmaceutical is illustrated in hexagonal form, as noted above, other geometries are contemplated.

Figures 4A, 4B, 4C:
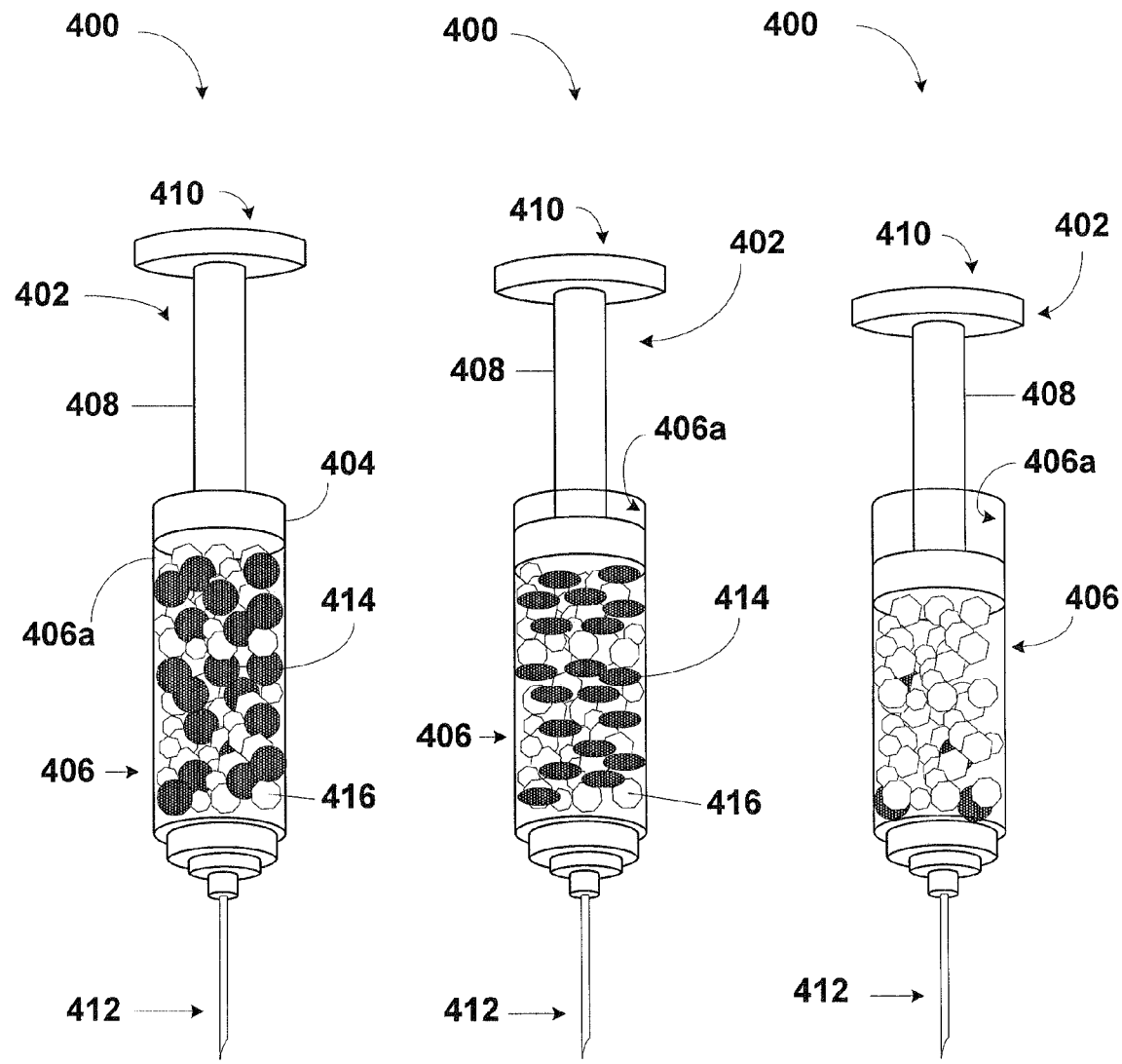
FIG. 4a is another partial cut-away view of a syringe in accordance with the present disclosure.
FIG. 4b is another partial cut-away view of a syringe in accordance with the present disclosure.
FIG. 4c is another partial cut-away view of a syringe in accordance with the present disclosure.

FIGS. 4a-4c illustrates one sequence of injection that may occur according to the present disclosure. The syringe 400 may include a plunger 402. The plunger may include a stopper 404, which may contact the interior surface 406a of the syringe body 406. For example, the stopper may form a relatively air and moisture tight seal with the syringe body preventing the introduction of environmental gasses or moisture. The plunger may also include an elongated member 408. The elongated member 408 may be removable from the plunger, such that during storage, the elongated member 408 may be removed from the syringe and plunger. For example, the elongated member may include one or more threads or other mechanical interlocks that may be used to join the elongated member to the stopper. The elongated member may also include a head 410. The head may allow for an increased surface area, as compared to the elongated member, for a user to apply pressure to the plunger. In some examples, pressure may be applied by a user or a mechanical device. The plunger 402 may be loaded into the syringe body 404.

As pressure may be applied to the plunger 402 in an axial direction towards the needle 412, pressure may be applied on the composition in the syringe displacing the plunger stopper 404 within the syringe body 406. The pressure may cause the microcapsules 414 to deform and start bursting, as illustrated in FIG. 4b. The pressures that are contemplated to provide for the microcapsules to burst include pressures of 10 psi to 5000 psi, including all values therein, in 1.0 psi increments. Preferably, the pressures may be in the range of 10 psi to 1000 psi, more preferably, in the range of 10 to 500 psi.

Upon bursting, the microcapsules release their solvent and the solvent combines with the pharmaceutical 416 composition, and the solvent and pharmaceutical may then pass through the needle 412 and into a subject (i.e., human or other mammal into which the pharmaceutical composition may be injected). In addition, as noted above, in those situations where the microcapsule shell is biodegradable and capable of being processed within the physiological environment, the shell material may be appropriately sized so that it may be also be injected through needle 412.

Figure 5:
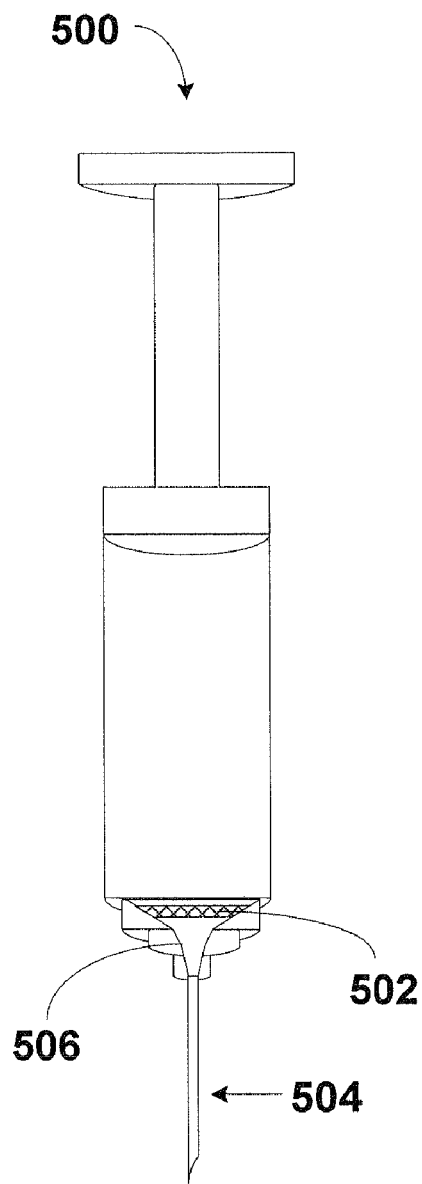
FIG. 5 is another partial cut-away view of a syringe in accordance with the present disclosure illustrating the location of a syringe filter.

In some examples, the syringe or other device may include a filter. The filter may prevent the ruptured microcapsules shells (or microcapsules that may not have ruptured) from passing through the needle tip and into the subject. As just noted, this may be the case when the shell material is such that it is not desirable that the shell material form part of the injection. FIG. 5 illustrates an embodiment of a cross-section of a syringe 500 wherein a filter 502 may be added to the syringe via a fitting positioned between the syringe and the needle 504. It may be appreciated that the fitting may be screwed or otherwise mechanically locked into place. The filter may be formed of a fabric or mesh. In some examples, the filter may be a polymeric material, such as a polyolefin, a fluropolymer such as polytetrafluorethylene, polyamide, etc. The filter may exhibit sufficient rigidity to prevent the filter from deflecting into the sidewalls of the outlet 506. It may therefore be appreciated that filtration may be configured to take place by controlling the size of the outlet 506 such that it may also provide removal of the microparticles or ruptured microparticles.

Figure 6:
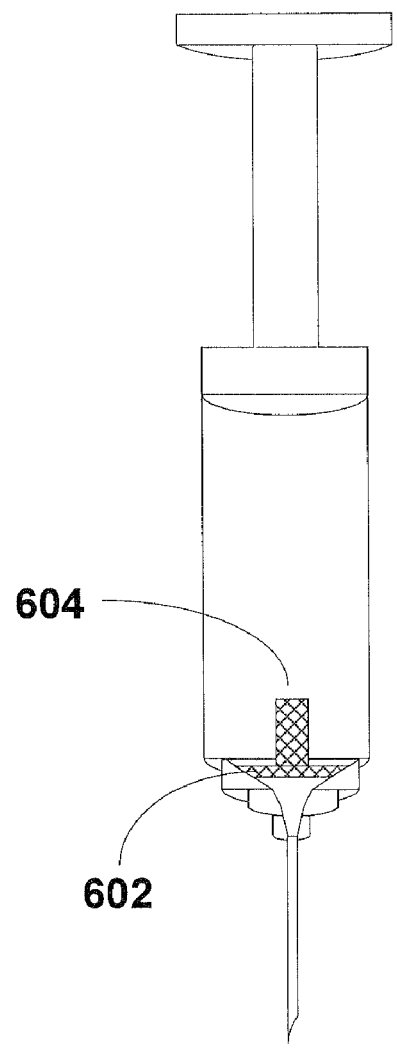
FIG. 6 is another partial cut-away view of a syringe in accordance with the present disclosure, illustrating the location and shape of a syringe filter.

FIG. 6 another example of a filter 602 that may be used in combination with a syringe and the composition disclosed herein. The filter may include a baffle or one or more projections 604 from the relatively planar filter surface illustrated in FIG. 5. It may be appreciated that as the microcapsules are crushed or burst, the microcapsule particles may stream into the filter and may occlude portions of the filter. Accordingly, as illustrated in FIG. 6, additional surface area may be provided in the filter, which may prevent the occlusion of the filter by the microcapsule shell material.

Accordingly, in some embodiments, as alluded to above, the filter may be porous and/or include a plurality of through holes that may allow for the solvent carrying the pharmaceutical to pass through the filter. The through holes may be relatively straight or may be relatively tortuous. The largest linear dimension of the filter holes may be selected to ensure that the insoluble microcapsule as well as the burst and insoluble microcapsule shell material and/or the heterogeneous phase material that was present inside the microcapsule does not pass through the filter. For example, the largest linear dimension of the filter holes may be 1.0% to 50.0% of the largest linear dimension of the microcapsule(s) that may be present, including all values and increments therein, such as 20% to 40%, 10% to 30%, etc. It may be appreciated that in other examples, the filter may be positioned at other areas within the syringe. For example, the filter may be provided within the syringe body itself at an end proximal to the needle or even towards the central portion of the syringe body.

In addition, contemplated herein is a method of filling the syringe. For example, as illustrated in FIG. 4 above, the microcapsules and pharmaceutical may be relatively evenly dispersed in the syringe body 406. In some examples, as illustrated in FIG. 7, the pharmaceutical 702 may be placed in the syringe body 704 proximal to the needle opening 706 and the microcapsules 708 above the pharmaceutical 702 distal to the needle opening 706. In other examples, as illustrated in FIG. 8, the opposite may be true, wherein the pharmaceutical 802 may be placed distal from the needle opening 806 in the syringe body 804 and the microcapsules 808 may be placed proximal to the needle opening 806. It may also be appreciated as illustrated in FIG. 9, and as alluded to above, the composition may include microcapsules 902 that are coated with the pharmaceutical 904 and the mixture may be relatively uniform.

Furthermore, it is contemplated that the syringe herein may include other features to enhance the mixing of the pharmaceutical with a given solvent after the solvent has been released from the microcapsule. For example, one or more baffles may be provided which may be present within the syringe body containing the microcapsules and pharmaceutical and/or the baffles may be positioned in the region between the filter and the syringe needle. In addition, it is contemplated that one may include, just prior to the region above the filter and/or after the filter, chambers that may cause the solvent to undergo some form of impingement mixing to further enhance the mixing of the pharmaceutical within a given solvent, prior to injection.

Once the syringe has been filled, it may be sealed and stored for a given period of time within a given container. In some examples, environmental gasses may be evacuated from the container after the pharmaceutical and microcapsules are placed in the syringe, to prevent introduction of excess air into the system. For example, vacuum may be applied to the container to withdraw the gasses from the container, which may therefore reduce the concentration of oxygen, and thereby improve the preservation of pharmaceutical activity.

As may be appreciated, the composition and method herein allows for the use of a solvent (e.g. water) sensitive pharmaceutical, even after a storage period of one or more hours, days, weeks, months or even years. Upon delivery, the pharmaceutical composition may be mixed with a released solvent and transported into the delivery site in solution form.

Accordingly, the present disclosure relates to an apparatus and method for combining a solid particulate with a solvent prior to an injection protocol within a syringe. The solid particulate may be a solid pharmaceutical compound and the microcapsules contain a solvent for such particulate. Upon application of pressure, the microcapsules may be configured to burst and release the solvent, thereby dispersing and/or partially dissolving the particulate. This then allows for the use of relatively unstable pharmaceutically active compounds in a device that requires relatively long storage times and the use of pharmaceutical compounds that are relatively stable in the dry state.

Working Example

Water capsules in the size range of 2.0-3.0 mm with a theoretical water loading targeting 55% by weight were prepared. The water capsules may be prepared by co-extrusion procedures. The fill material (water) may be pumped through an inner nozzle while the shell formulation consisting of polyethylene (PE), paraffin wax and Piccolyte® (polyterpene) resin may be pumped through the outer nozzle. The co-extrusion nozzle is then inserted into a tertiary pipe through which a carrier fluid (water, alcohol, polyethylene oxide) is pumped. The carrier fluid assists in breaking up the extruded coaxial jet to form the capsules and also assists in congealing of the wax shell formulation. The resulting capsules may then be collected by filtration and the carrier fluid may be recycled back to the submerged nozzle assembly.

The water capsules were then loaded into syringes (1.0 and 3.0 mL volumes) and the plunger depressed to determine the amount of water expelled. The injected water was collected in a tarred weight boat on an analytical balance. The results of the water injection study are summarized in Table I.

capsules occupied a volume of 1.2 mL. The working example therefore confirms that one may provide an injector that allows for the combination of a solid particulate (e.g. a pharmaceutical substance) with microcapsules containing a solvent or heterogeneous phase material including the solvent, where the microcapsules may be configured to open upon application of pressure.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. An injector allowing for the combination of a solvent and a solid comprising:
   (a) a housing containing a solid particulate, said solid particulate having a diameter of 0.1 microns to 5.0 mm;
   (b) microcapsules containing:
      i. a solvent for said particulate; or
      ii. a heterogeneous phase material including said solvent;
   wherein said microcapsules have an average mean particle size of 100 nm to 10,000 microns and wherein said microcapsules are configured to open upon application of pressure including an outlet capable of filtration, wherein said filtration is configured to prevent microcapsules and/or opened microcapsules and/or heterogenous phase material from passing through said outlet and exiting said injector.

2. The injector of claim 1, wherein said microcapsules include a shell material that is biodegradable and capable of being processed within the physiological environment.

3. The injector of claim 2 wherein said shell material comprises one or more of the following: poly(lactide), poly(glycolide), poly(lactide-glycolide) copolymers, polycaprolactones, polyanhydrides, glycerides, fatty acids, and cellulose derivatives.

4. The injector of claim 1 wherein said solid particulate is capable of dissolving in said solvent within the time period of less than or equal to 10.0 seconds.

TABLE I

| Injection* | Tared weight (Empty Syringe) | Gross weight (Loaded Syringe) | Net weight of Capsules Loaded | Weight of water injected | Ratio of water injected to Capsules loaded | Wt. Of syringe with crushed capsules after injection | Wt. of material remaining in syringe** |
|---|---|---|---|---|---|---|---|
| 1 | 2.598 g | 3.135 g | 0.537 g | 0.272 g | 0.51 | 2.860 g | 0.262 g |
| 2 | 2.530 g | 3.063 g | 0.533 g | 0.266 g | 0.50 | 2.793 g | 0.263 g |
| 3 | 2.543 g | 3.112 g | 0.569 g | 0.272 g | 0.48 | 2.825 g | 0.285 g |
| 4 | 3.205 g | 5.008 g | 1.803 g | 0.748 g | 0.41 | 4.236 g | 1.031 g |

*Injection 1-3 used a 1 mL BD Tuberculin, Skip-Tip, Disposable Syringe (filled to 1 mL level with beads)
*Injection 4 used a 3 mL BD Luer-Lok, Disposable Syringe (filled to 3 mL level with beads)
**The vol. of material remaining in syringe after injection was 0.25 mL for Injection 1-3 and 1.2 mL for Injection 4.

The amount of water injected was approximately half the weight of the capsules loaded into the syringe. Based on the theoretical loading of 55% water in the capsules, most of the water was injected. There is some water remaining in the syringe because of the ruptured capsules preventing complete depression of the plunger. For the 1.0 mL syringe, the ruptured capsules occupied a volume of 0.25 mL and the weight of the material remaining in the syringe is listed in the last column of Table 1. For the 3.0 mL syringe, the ruptured 5. The injector of claim 1 wherein the solid particulate is capable of dissolving within the time period of less than or equal to 2.0 seconds.

6. The injector of claim 1 wherein said particulate has a solubility in said solvent of 0.1% (wt.) to 99.9% (wt.).

7. The injector of claim 1 wherein said microcapsules are configured to open upon application of a pressure of 10 psi to 5000 psi.

8. The injector of claim 1 wherein said particulate comprises a pharmaceutical substance.

9. The injector of claim 8 wherein said pharmaceutical substance comprises oximes having the structure below:

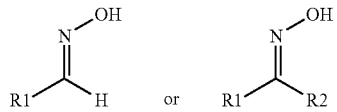

where R1 is an organic side chain and R2 is either hydrogen or another organic group.

10. The injector of claim 8 wherein said pharmaceutical substance comprises a 1,1'-methylenebis[4-(hydroxyimino)methyl]-pyridinium salt.

11. The injector of claim 8 wherein said pharmaceutical substance comprises an antimuscarinic.

12. The injector of claim 1 wherein said particulate comprises an antibiotic, a vaccine, an antigen, a protein, an enzyme, or a gene.

13. The injector of claim 1 wherein said solvent in said microcapsules contain water.

14. The injector of claim 1 wherein said heterogeneous material comprises a hydrogel.

15. The injector of claim 1 wherein said particulate includes a surface active agent.

16. The injector of claim 1 wherein said particulate includes sucrose, lactose, fructose, sodium chloride or a hydrocolloid.

17. The injector of claim 1 wherein said outlet includes a filter to prevent said microcapsules and/or opened microcapsules from exiting said injector.

18. The injector of claim 1 wherein said microcapsules include a dye.

19. An injector allowing for the combination of a solvent and a solid comprising:
  (a) a housing containing a solid particulate of a pharmaceutical substance, said substance having a diameter of 0.1 microns to 5.0 mm;
  (b) microcapsules containing:
    i. a solvent for said particulate; or
    ii. a heterogeneous phase material including said solvent;
  wherein said microcapsules have an average mean particle size of 100 nm to 10,000 microns and wherein said microcapsules are configured to open upon application of pressure and said solid particulate is capable of dissolving in said solvent within the time period of less than or equal to 10 seconds and said microcapsules are configured to open upon application of a pressure of 10 psi to 5000 psi.

20. The injector of claim 19 wherein said microcapsules include a shell material that is biodegradable and capable of being processed within the physiological environment.

21. The injector of claim 19 including an outlet capable of filtration wherein said filtration is configured to prevent microcapsules and/or opened microcapsules and/or heterogenous phase material from passing through said outlet and exiting said injector.

22. A method for injection of a pharmaceutical comprising supplying
  (a) an injector including a housing for solid particulate, said solid particulate having a diameter of 0.1 microns to 5.0 mm;
  (b) microcapsules containing:
    i. solvent for said particulate; or
    ii. a heterogeneous phase material including said solvent;
  wherein said microcapsules have an average mean particle size of 100 nm to 10,000 microns and wherein said microcapsules are configured to open upon application of pressure;
  applying pressure to said microcapsules thereby causing said microcapsules to open and release said solvent wherein said pharmaceutical particulate is dispersed and/or partially dissolves in part in said solvent.

23. The method of claim 22 wherein said microcapsules include a shell that is biodegradable and capable of being processed within the physiological environment.

24. The method of claim 22 wherein said injector includes an outlet capable of filtration, wherein said filtration is configured to prevent microcapsules and/or opened microcapsules and/or heterogeneous phase material from passing through said outlet and exiting said injector.

25. An injector allowing for the combination of a solvent and a solid comprising:
  (a) a housing containing a solid particulate, said solid particulate having a diameter of 0.1 microns to 5.0 mm;
  (b) microcapsules containing:
    i. a solvent for said particulate; or
    ii. a heterogeneous phase material including said solvent;
  wherein said microcapsules have an average mean particle size of 100 nm to 10,000 microns and wherein said microcapsules are configured to open upon application of pressure wherein said particulate has a solubility in said solvent of 0.1% (wt.) to 99.9% (wt.).

* * * * *